(12) United States Patent
Caruso et al.

(10) Patent No.: US 6,194,422 B1
(45) Date of Patent: *Feb. 27, 2001

(54) ANTHRACYCLINE DERIVATIVES

(75) Inventors: Michele Caruso, Milan; Daniela Faiardi, Pavia; Tiziano Bandiera, Gambolò Pavia; Jacqueline Lansen; Antonino Suarato, both of Milan, all of (IT)

(73) Assignee: Pharmacia & Upjohn SpA, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/341,703

(22) PCT Filed: Jan. 9, 1998

(86) PCT No.: PCT/EP98/00152

§ 371 Date: Jul. 27, 1999

§ 102(e) Date: Jul. 27, 1999

(87) PCT Pub. No.: WO98/32754

PCT Pub. Date: Jul. 30, 1998

(30) Foreign Application Priority Data

Jan. 27, 1997 (GB) .................................................. 9701628

(51) Int. Cl.$^7$ .................... A61K 31/4375; C07D 471/08; C07D 487/08
(52) U.S. Cl. ............................ 514/279; 514/282; 546/43; 546/44; 546/45
(58) Field of Search ..................................... 514/279, 281, 514/282; 546/43, 44, 45

(56) References Cited

U.S. PATENT DOCUMENTS 5,731,313   3/1998   Suarato et al. .
5,985,887 * 11/1999  Caruso et al. ........................ 514/278

* cited by examiner

Primary Examiner—Alan L. Rotman
Assistant Examiner—Rita Desai
(74) Attorney, Agent, or Firm—Oblon, Spivak, McClelland, Maier & Neustadt, P.C.

(57) ABSTRACT

The present invention provides imino aza-anthracyclinones and a method of treating amyloidoses using the same.

16 Claims, No Drawings

ANTHRACYCLINE DERIVATIVES

BACKGROUND OF THE INVENTION

1. Field of the Invention

The present invention relates to imino aza-anthracyclinone derivatives, their use for the treatment of amyloidoses, methods for their preparation and pharmaceutical compositions containing them.

2. Description of the Background

The relationship between amyloidosis, cell death and loss of tissue function appears to be of relevance for different type of disorders including some neurodegenerative disorders. Therefore, the prevention of amyloid formation and/or the induction of amyloid degradation can be an important therapeutic strategy for all pathological disorders associated with amyloidosis including peripheral amyloidoses and neurodegenerative disorders of the Alzheimer's type.

SUMMARY OF THE INVENTION

The present invention provides imino aza-anthracyclinones and their use in the treatment of amyloidoses. This new class of molecules is derived from a parent compound named anthrazalone that is characterized by the presence of an anthraquinone system fused to a bridged heterocyclic ring and whose structure is depicted below:

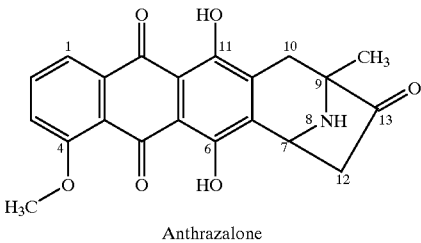

Anthrazalone

DETAILED DESCRIPTION OF THE PREFERRED EMBODIMENTS

Anthrazalone can be considered as a member of a new class of molecules that are related to 8-aza-anthracyclinones and which can be referred to as anthrazalinones.

The compounds provided by the present invention are characterized by the presence of an imino functionality on the bridged heterocyclic ring.

More particularly, the present invention provides an anthrazalinone derivative of formula 1

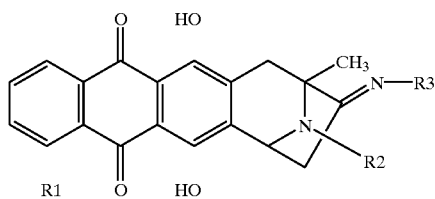

wherein:

$R_1$ is selected from:
hydrogen,
hydroxyl,
$C_{1-16}$ alkyl,
$C_{1-16}$ alkoxyl,
$C_{3-8}$ cycloalkoxyl,
halogen,
amino which may be unsubstitued or mono- or di-substituted by acyl, trifluoroacyl, aralkyl, aryl,
$OSO_2(R_4)$ wherein $R_4$ is alkyl or aryl;

$R_2$ is selected from hydrogen,
$R_B$—$CH_2$— wherein $R_B$ represents an aryl group, a heterocyclyl group or a group of formula $R_C$—CH=CH— wherein $R_C$ is hydrogen, $C_{1-16}$ alkyl, $C_{2-8}$ alkenyl or $C_{3-8}$ cycloalkyl,
$C_{1-16}$ alkyl,
$C_{3-8}$ cycloalkyl,
aryl—$C_1$-$C_{16}$—alkyl,
aryloxy-$C_1$-$C_{16}$—alkyl
acyl of formula —$C(R_5)$=O wherein $R_5$ is selected from
hydrogen,
$C_{1-16}$ alkyl,
$C_{2-16}$ alkenyl,
$C_{3-8}$ cycloalkyl,
aryl,
heterocyclyl,
an acyl residue of an amino acid, $R_3$ is selected from:
a group of formula OR, wherein $R_6$ represents
hydrogen,
$C_{1-16}$ alkyl,
$C_{2-16}$ alkenyl,
$C_{3-8}$ cycloalkyl,
aryl—$C_1$-$C_6$—alkyl,
aryl,
a group of formula $NR_7R_8$ wherein $R_7$ and $R_8$, which can be the same or different, represent
hydrogen,
$C_{1-16}$ alkyl,
aralkyl,
$C_{2-16}$ alkenyl,
$C_{3-8}$ cycloalkyl,
heterocyclyl,
acyl of formula —$C(R_5)$=O wherein $R_5$ is as above defined,
or $R_7$ and $R_8$ together with the N atom to which they are attached, represent heterocyclyl,
with the proviso that when $R_1$ is a methoxyl group and $R_3$ is a hydroxyl group then $R_2$ is not 4-pyridinmethyl,
or a pharmaceutically acceptable salt thereof.

Preferred compounds of formula 1 are those wherein:
$R_1$ is selected from hydrogen, hydroxy, methoxy,
$R_2$ is selected from hydrogen, methyl, allyl, benzyl, 3-bromobenzyl, 4-trifluoromethylbenzyl, 4-methoxybenzyl, (4-benzyloxy)benzyl, 3,4-dimethoxybenzyl, 3,5-dit.butyl-4-hydroxybenzyl, pyridinmethyl, glycyl, alanyl, cisteyl, nicotinoyl,
$R_3$ is selected from hydroxy, methoxy, ethoxy, benzyloxy, pyridinmethyloxy, methyl amino, dimethylamino, benzylamino, 4-morpholinyl, 4-methylpiperazinyl.

An "alkyl" group or moiety is typically a $C_1$-$C_{16}$ alkyl group or moiety. A $C_1$-$C_{16}$ alkyl group or moiety includes both straight and branched chain alkyl groups or moieties. Preferably, a $C_1$-$C_{16}$ alkyl group or moiety is a $C_1$-$C_{12}$ alkyl group or moiety such as heptyl, octyl, nonyl, decyl, undecyl or dodecyl or a branched chain isomer thereof. Preferably, a $C_1$-$C_{12}$ alkyl group or moiety is a $C_1$-$C_6$ alkyl group or moiety such as methyl, ethyl, propyl, isopropyl, butyl, t-butyl, isobutyl, pentyl, hexyl, or isohexyl or a branched chain isomer thereof.

The alkyl groups and moieties discussed above may be substituted with one or more substituent selected from cycloalkyl, heterocyclyl, halogen, $CF_3$, hydroxy, alkoxy, aryloxy, amino, mono- or di-alkylamino, carboxy, alkyloxycarbonyl.

The term "alkenyl" as used herein includes both straight and branched chain radicals of up to 16 carbons such as nonenyl, decenyl and dodecenyl. Preferred alkenyl groups have up to 8 carbon atoms. Examples include allyl, butenyl, hexenyl, octenyl.

The term "cycloalkyl" as used herein means a cycloalkyl group having 3 to 8 carbons, preferably from 3 to 5 carbon atoms. Examples include cyclopropyl, cyclopentyl, cyclohexyl, cycloheptyl and cyclooctyl.

An "aryl" group or moiety includes both monocyclic and bicyclic aromatic groups or moieties typically containing from 6 to 10 carbons in the ring portion, such as phenyl or naphthyl, optionally substituted by one or more substituent, preferably by one, two or three substituents selected from $C_{1-6}$ alkyl, $C_{1-6}$ alkoxy, trifluoromethyl, halogen, hydroxy or aryloxy.

The term "heterocyclyl" as employed herein is a 3-, 4-, 5- or 6-membered, saturated or unsaturated heterocyclic ring containing at least one heteroatom selected from O, S and N, which is optionally fused to a second 5- or 6-membered, saturated or unsaturated heterocyclyl group or to a said cycloalkyl group or aryl group.

Examples of heterocyclyl groups are pyrrolyl, pyrazolyl, imidazolyl, triazolyl, tetrazolyl, oxazolyl, isoxazolyl, thiazolyl, isothiazolyl, thiadiazolyl, thienyl, furanyl, pyranyl, pyridinyl, dihydropyridinyl, piperidinyl, piperazinyl, pyrazinyl, pirimidinyl, pyridazinyl, pyrrolidinyl, morpholinyl, benzimidazolyl, benzothiazolyl or benzoxazolyl group.

The term "halogen" as used herein means fluorine, chlorine, bromine or iodine.

The term "aralkyl" as used herein refers to alkyl groups as previously discussed substituted by a said aryl group, for example benzyl, phenethyl, diphenylmethyl and triphenylmethyl.

The term "alkoxy", "aryloxy" or "cycloalkoxyl" as used herein includes any of the above alkyl, aralkyl or cycloalkyl groups linked to an oxygen atom.

The term "aryloxyalkyl" as used herein means any alkyl as discussed above linked to an aryl as discussed above by an oxygen atom, for example phenoxyethyl or phenoxypropyl.

The term "amino acid" as used herein means a naturally occuring amino acid, for example glycine, alanine, cysteine, phenylalanine, tyrosine and the like.

An acyl group is typically a $C_1$–$C_{10}$ acyl group, for example a $C_1$–$C_6$ acyl group such as a methanoyl, ethanoyl, propanoyl, butanoyl, t-butanoyl, sec-butanoyl or hexanoyl group.

This invention also includes all the possible isomers of compounds of the formula (1) and mixtures thereof, for example diastereoisomeric mixtures and racemic mixtures. Thus, the stereocenters at the 7-position and the 9-position may be in the R- or the S- configuration (or both, i.e. a mixture of stereoisomers is present). Similarly the oximes and hydrazones may be in the form of syn or anti isomers or a mixture of syn and anti isomers.

The present invention also provides the salts of those compounds of formula 1 that have salt-forming groups, especially the salts of the compounds having a carboxylic group or a basic group (e.g. an amino group).

The salts are typically physiologically tolerable, or pharmaceutically acceptable, salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulfuric acid, mono- and dicarboxylic acids and sulfonic acids (e.g. acetic, trifluoroacetic, tartaric, methanesulfonic, p-toluensulphonic acid). Compounds of formula 1 in which $R_1$, $R_2$ and $R_3$ are as defined above can be prepared by:

(a) reacting a compound of formula 2

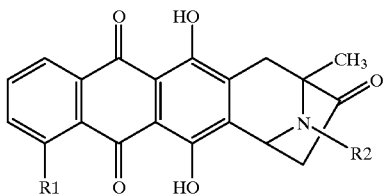

wherein $R_1$ and $R_2$ are as defined above, with a compound of formula $R_3$—$NH_2$ wherein $R_3$ is as defined above, and (b) if desired, converting the resultant compound of formula 1 into a different compound of formula 1 by an appropiate chemical reaction, and/or (c) converting the compound of formula 1 into a pharmaceutically acceptable salt thereof.

A compound of formula 2 is typically reacted with a compound of formula $R_3$—$NH_2$ or $R_3$—$NH_2$ . HA, wherein $R_3$ is as defined above and HA represents an inorganic acid, typically hydrochloric or sulfuric acid, in an organic solvent which is generally selected from methanol, ethanol, dioxane or toluene. The compound $R_3$—$NH_2$ or $R_3$—$NH_2$ . HA is typically present in a 2 to 5 fold excess. When a compound of formula $R_3$—$NH_2$ . HA is used, the reaction is carried out in the presence of an equimolar amount of an organic or inorganic base. The base is typically selected from sodium acetate and sodium or potassium hydrogen carbonate. The reaction is typically carried out for a period of 1 to 24 hours and takes place from room temperature to about 100° C. The solvent is typically ethanol and the reaction is typically carried out at 80° C. for two to four hours.

Compounds of formula $R_3$—$NH_2$ or $R_3$—$NH_2$ . HA are generally commercially available or they can be prepared in analogy to known procedures reported in the literature (see, for example, *Houben-Weyl, Methoden der Organischen Chemie*, vol E 16a, Georg Thieme Verlag, Stuttgart 1990).

Compounds of formula 1, in which $R_1$ and $R_2$ are as defined above and $R_3$ is $OR_6$, wherein $R_6$ is hydrogen, can be converted into compounds of formula 1, in which $R_1$ and $R_2$ are as defined above and $R_3$ is $OR_6$, wherein $R_6$ does not represent hydrogen or aryl, following known procedures described in the literature (see, for example, *J. Am. Chem. Soc.* 1949, 71, 3021 or *Farmaco, Ed. Sci.* 1990, 45, 1013).

Compounds of formula 1, in which $R_1$ is as defined above, $R_2$ is hydrogen and $R_3$ is $OR_6$, wherein $R_6$ does not represent hydrogen, can be converted into compounds of formula 1, in which $R_1$ is as defined above, $R_2$ is an acyl group of formula—$C(R_5)$=O, wherein $R_5$ is as defined above, and $R_3$ is $OR_6$, wherein $R_6$ does not represent hydrogen, following known acylation procedures. The conversion is preferably carried out by reacting a compound of formula 1, in which $R_1$ is as defined above, $R_2$ is hydrogen and $R_3$ is $OR_6$, wherein $R_6$ does not represent hydrogen, with an acid of formula $R_5$—COOH in the presence of a condensing agent, such as diisopropylcarbodiimide, dicyclohexylcarbodiimide or 2-ethoxy-1-ethoxycarbonyl-1,2-dihydroquinone (EEDQ). Preferred reaction conditions encompass the use of an anhydrous solvent such as dichloromethane or dimethylformamide at room temperature for a period of from 4 to 24 hours.

A compound of formula 1, in which $R_1$, $R_2$ and $R_3$ are as defined above, can be converted into a pharmaceutically acceptable salt by dissolving the free base in a proper organic solvent like dichloromethane, methanol, ethanol or dioxane and adding a solution of a pharmaceutically acceptable organic or inorganic acid in methanol, ethanol or dioxane. The resulting salt of compound 1 is obtained by evaporation or concentration of the solution or the salt is precipitated by addition of diethyl ether to the salt solution.

When necessary, at any stage of the process all the possible resultant diastereoisomeric mixtures and racemic mixtures may be separated by conventional methods. The oximes and hydrazones may be obtained as mixtures of syn and anti isomers or as a single isomer; the mixtures can be separated into the single syn and anti isomers by known methods, for example by chromatography.

Compounds of formula 2 in which $R_1$ is as defined above and $R_2$ represents a residue $R_BCH_2$ as above defined can be prepared by reacting a compound of formula 3

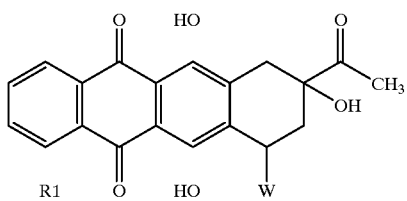

3 wherein $R_1$ is as above defined and W represents a leaving group, with an amine of formula

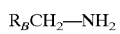

wherein $R_B$ is as defined above.

Suitable W groups include O-saccharides such as O-daunosaminyl derivatives, O-acyl such as O-trifluoroacetyl or O-(p-nitrobenzoyl) or O-ethoxycarbonyl and O-acetal such as O-tetrahydropyranyl (O-THP). Preferred amines of formula $R_BCH_2$—$NH_2$ include allylamine and alkylaryl amines, for example benzylamine, 3,4-dimethoxybenzyl amine or pyridinmethylamine.

A compound of formula 3 is typically reacted with a 1 to 10 fold excess of an amine of formula $R_BCH_2$—$NH_2$ as above defined. The reaction may take place in a suitable organic solvent such as dichloromethane or pyridine. An organic base such as pyridine may be present. The reaction may take place for a period of 6 to 48 hours, typically at from –10° C. to room temperature.

Preferably a four fold excess of an amine of formula $R_BCH_2$—$NH_2$ is used. The solvent is most typically pyridine. Preferred reaction conditions are room temperature for 12 to 24 hours.

Compounds of formula 2 in which $R_1$ is as defined above and $R_2$ represents hydrogen may be prepared, for example, by deblocking a compound of formula 2 in which $R_1$ is as defined above and $R_2$ is 3,4-dimethoxybenzyl by means of 2,3-dichloro-5,6-dicyano-1,4-benzoquinone (DDQ). Preferred conditions encompass the use of an equivalent amount of DDQ in a mixture of dichloromethane and water (typically in a ratio 20:1 by volume). The reaction is typically conducted at room temperature and time for from 1 to 6 hours.

Compounds of formula 2 in which $R_1$ is as defined above and $R_2$ represents a $C_{1-16}$ alkyl, $C_{3-8}$ cycloalkyl, said aralkyl or said aryloxyalkyl group may be prepared from compounds of formula 2 wherein $R_1$ is as defined above and $R_2$ represents hydrogen by standard alkylation procedures.

For example 8-N-alkyl-, -alkenyl-, -cycloalkyl-, -aralkyl- or aryloxyalkyl-anthrazalinones of formula 2 are preferably prepared by reacting a compound of formula 2 in which $R_1$ is as defined above and $R_2$ is hydrogen with a group $R_2$-X wherein $R_2$ is $C_{1-16}$ alkyl, $C_{3-8}$ cycloalkyl, said aralkyl or said aryloxyalkyl and X is a leaving group such as a halogen, O—$SO_2$—$CF_3$, O—$SO_2$—$CH_3$ or O—$SO_2$—$C_6H_4$—$CH_3$. Preferably X is halogen, more preferably iodine or bromine. Typically, the reaction takes place in the presence of a suitable organic or inorganic base. Preferred conditions encompass the use of from 2 to 10 fold excess of $R_2$-X in an organic solvent such as dichloromethane or dimethylformamide in the presence of triethylamine, ethyl diisopropylamine or sodium hydrogen carbonate at temperature from 40 to 80° C. for 4 to 24 hours.

Compounds of formula 2 wherein $R_1$ is as above defined and $R_2$ is an acyl group of formula —$C(R_5)$=O wherein $R_5$ is as above defined are preferably prepared by reacting a compound of formula 2 in which $R_2$ is hydrogen with an acyl derivative of formula $R_5$—CO—Hal or $(R_5CO)_2O$ wherein $R_5$ is as above defined and Hal is halogen, preferably chlorine. Preferred conditions encompass use of from 2 to 10 fold excess of acyl derivative in an organic solvent such as dichloromethane or dimethylformamide at temperature from –10 to 40° C. and time from 1 to 24 hours.

In a further example, compounds of formula 2 wherein $R_1$ is as above defined and $R_2$ is an acyl group of formula —$C(R_5)$=O, wherein $R_5$ is as above defined, or an acyl residue of an amino acid, may be prepared by reacting an anthrazalinone of formula 2 in which $R_2$ is hydrogen with an acid derivative of formula $R_5$—COOH or with a suitably protected amino acid in the presence of a condensing agent such as dicyclohexylcarbodiimide or 2-ethoxy-1-ethoxycarbonyl-1,2-dihydroquinone (EEDQ) in an anhydrous organic solvent. Preferred conditions encompass the use of from 1 to 4 fold excess of the acid or the protected amino acid in a dry organic solvent such as dimethylformamide. An equivalent amount of EEDQ is typically used at room temperature for 15 hours.

Compounds of formula 3 are available from natural sources or may be prepared by following known synthetic methods starting from known anthracyclines or anthracyclinones.

For example, 7-O-saccharide in which the sugar is daunosaminyl may be derived from a natural source, such as daunorubicin, or may be prepared by means of synthetic modification of the same.

Other aglycones functionalized at position C-7 may be prepared by means of well known procedures.

For example, 7-O-THP derivatives of formula 3 (W=O—THP) can be prepared by reacting an aglycone of formula 4:

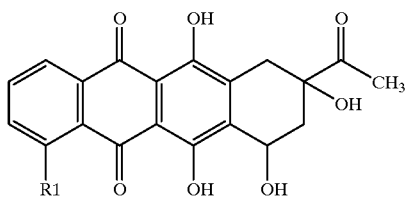

4 with 3,4-dihydro-2H-pyrane in an organic solvent and in the presence of an acid catalyst at room temperature for 1 to 4 hours. Preferred conditions encompass dissolving an aglycone of formula 4 in dichloromethane and reacting the same with 4 equivalents of 3,4-dihydro-2H-pyrane in the presence of a catalytic amount of canforsulfonic or p-toluensulfonic acid at room temperature for 4 hours. The 7-O-THP derivative is recovered by washing the reaction mixture with aqueous sodium hydrogen carbonate, water and then removing the solvent under reduced pressure.

7-O-acyl derivatives of formula 3 can be prepared by reacting an aglycone of formula 4 with a suitable carboxylic acid, acid anhydride or acyl chloride in an organic solvent and in the presence of a base at temperature from −10 to room temperature and time for 1 to 6 hours.

For example a 7-O-acetyl derivative of formula 3 (W=O—COCH$_3$) can be prepared by reacting an aglycone of formula (4) with acetic anhydride in an organic solvent such as dichloromethane and in the presence of an organic base such as pyridine. The compound can be recovered by precipitation of the crude material in an apolar solvent such as hexane.

Some of the starting materials for the preparation of compounds of formula 2 are known, others may be prepared starting from known anthracyclines or anthracyclinones by means of known procedures.

For example, the following anthracyclines are known and can be represented by the same formula 3: daunorubicin (3a: $R_1$=OCH$_3$, W=O-daunosaminyl), 4-demethoxydaunorubicin (3b: $R_1$=H, W=O-daunosaminyl), 4-aminodaunorubicin (3c: $R_1$=NH$_2$, W=O-daunosaminyl). Also some 7-O-derivatives of formula 3 are known, for example 7-O-ethoxycarbonyldaunomycinone (3d: $R_1$=OCH$_3$, W=O—COOC$_2$H$_5$), 7-O-THP-daunomycinone (3e: $R_1$=OCH$_3$, W=O-THP), 7-O-acetyldaunomycinone (3f: $R_1$=OCH$_3$, W=O—COCH$_3$). The compounds of the present invention are characterized by high inhibitory activity on the formation of amyloid deposits by amyloidogenic proteins and are able to induce the degradation of existing amyloid deposits.

The term amyloidosis indicates a group of diseases whose common characteristic is the tendency of particular proteins to aggregate and precipitate, in the form of aggregates of insoluble fibrils, in the extracellular space. The aggregated protein can thus cause structural and functional damage to organs and tissues. The classification of amyloid and amyloidosis has been recently revised in Bulletin of the World Health Organisation 1993, 71(1), 105.

All the different types of amyloid share a common ultrastructural organization in anti-parallel β-pleated sheets despite the fact that they contain a variety of widely differing protein subunits [see: Glenner G. G., New England J. Med. 1980, 302, 1283]. AL amyloidosis is caused by peculiar monoclonal immunoglobulin light chains which form amyloid fibrils. These monoclonal light chains are produced by monoclonal plasma cells with a low mitotic index which accounts for their well known insensitivity to chemotherapy. The malignacy of these cells consists in their protidosynthetic activity.

The clinical course of the disease depends on the selectivity of organ involvement; the prognosis can be extremely unfavourable in case of heart infiltration (median survival<12 months) or more benign in case of kidney involvement (median survival approx. 5 years).

Molecules that can block or slow amyloid formation and increase the solubility of existing amyloid deposits seems the only reasonable hope for patients with AL amyloidosis. Furthermore, since the supramolecular organization of the amyloid fibrils is the same for all types of amyloid, the availability of a drug that interferes with amyloid formation and increases the solubility of existing deposits, allowing clearance by normal mechanisms, could be of great benefit for all types of amyloidoses, including amyloidoses of the central nervous system such as Alzheimer's disease and other pathologies.

Indeed, one of the major pathological feature of Alzheimer's Disease (AD), Downs Syndrome, Dementia pugilistica and Cerebral amyloid angiopathy is the deposition of a 39–43 amino acid peptide, referred to as the amyloid β-peptide (Aβ), in the form of insoluble, protease resistant amyloid deposits in cerebral parenchyma and vessel walls. This marker is associated with neuronal cell loss in cerebral cortex, limbic regions and subcortical nuclei. Several studies have shown that selective damage to various neuronal systems and synapse loss in the frontal cortex correlate with cognitive decline. The pathogenesis and the molecular basis of the neurodegenerative processes in AD is not well understood, but the precipitation of Aβ peptides in the form of amyloid deposits in the brain could play a central role in the genesis of the disease. In fact, in vitro neurotoxic effects of Aβ peptides on different cell systems, including primary cultured neurons, have been reported by many investigators [Yankner et al., *Science* 1989, 245, 417; Roher et al., *Biochem. Biophys. Res. Commun.* 1991, 174, 572; Koh et al., *Brain Res.* 1990, 533, 315; Copani et al., *NeuroReport*

1991, 2, 763; Mattson et al., *J. Neurosci.* 1992, 12, 376; Mattson et al., *Brain Res.* 1993, 621, 35; Pike et al., *J. Neurosci.* 1993, 13, 1676;].

Furthermore, the segregation of familiar AD with mutations in the amyloid precursor protein (APP) gene suggests a potential pathogenetic function of β-amyloid deposition in AD [Mullan M. et al. *TINS* 1993, 16, 392]. Indeed, the soluble form of Aβ peptides is produced in vivo and in vitro as a result of normal cellular metabolism [Haass et al. *Nature* 1993, 359, 322].

The neurotoxicity of Aβ peptides has been associated with their fibrillogenic properties. Studies with synthetic peptides indicate that hippocampal neurons were insensitive to exposure to fresh Aβ1-40 or Aβ1-42 solution for 24 hours while their viability decreased when they were exposed to Aβ1-40 or Aβ1-42 previously stored in saline solution for 2–4 days at 37° C. to allow the peptide aggregation [Lorenzo and Yankner *PNAS* 1994, 91, 12243].

On the other hand, non-congophilic "preamyloid" formations, containing non-aggregated Aβ peptides, were not associated with neuronal alteration [Tagliavini et al. *Neurosci. Lett.* 1988, 93, 191].

The neurotoxic and fibrillogenic properties of full length Aβ peptides has also been found in a shorter fragment spanning residues 25–35 (Aβ25–35) of the Aβ sequence. Chronic but not acute exposure of hippocampal neurons to micromolar concentration of Aβ25–35 induced neuronal death by the activation of a mechanism of programmed cell death known as apoptosis [Forloni et al. *NeuroReport* 1993, 4, 523]. Here again, neurotoxicity was associated with the self aggregating property of Aβ25–35.

Other neurodegenerative disorders such as spongiform encephalopathy (SE) are characterized by neuronal death and extracellular deposition of amyloid, in this case originated from Prion (PrP) protein. In analogy with the observation that β-amyloid is neurotoxic, the effects of synthetic peptides homologous to different segments of PrP on the viability of primary rat hippocampal neurons have been investigated. The chronic application of a peptide corresponding to PrP fragment 106–126 induced neuronal death by apoptosis while under the same conditions the scrambled sequence of PrP 106–126 did not reduce cell viability [Forloni et al., *Nature* 1993, 362, 543]. PrP 106–26 was shown to be highly fibrillogenic in vitro and when stained with Congo red, the peptide aggregates showed green birefringence indicative of the β-sheet conformation characteristic of amyloid.

The ability of compounds 1 to inhibit the formation of amyloid fibrils was assessed through the light scattering and thioflavin T assays.

The light scattering assay was performed as below described.

Aβ25–35 (GSNKGAIIGLH) and PrP 106–126 (KTNMKHMAGAAAAGAWGGLG) were synthesized using solid phase chemistry by a 430A Applied Biosystems Instruments and purified by reverse-phase HPLC (Beckman Inst. mod 243) according to Forloni et al., *Nature* 1993, 362, 543.

Light scattering of the peptide solutions was evaluated by spectrofluorimetry (Perkin Elmer LS 50B), excitation and emission were monitored at 600 nm.

When Aβ fragment 25–35 and PrP 106–126 were dissolved at a concentration of 0.5 to 1 mg/ml (0.4–0.8 mM and 0.2–0.4 mM respectively) in a solution of 10 mM phosphate buffer pH 5, they spontaneously aggregate within an hour.

When compounds 1 were added to the solutions of the peptides at equimolar concentration a prevention of the aggregation was observed.

The thioflavin T assay measures the ability of a test compound to inhibit the aggregation of a peptide into amyloid fibrils. The amyloid formation is quantified through the thioflavin T fluorescence. Thioflavin T binds specifically to amyloid fibrils and this binding produces a shift in its absorption and emission spectra: the intensity of the fluorescence signal is directly proportional to the mass of amyloid formed.

The assay was performed as described below.

Stock solutions of Aβ 25–35 peptide were prepared by dissolving the lyophilized peptide in dimethyl sulfoxide (DMSO) at a concentration of 7.07 mg/ml.

Aliquotes of this solution were dissolved in 50 mM phosphate buffer pH 5 so as to obtain a final peptide concentration of 100 $\mu$M and incubated for 24 hours at 25° C. with or without 30 $\mu$M test compound in a final volume of 113 $\mu$l. The compounds were previously dissolved in DMSO at a concentration of 3.39 mM and then diluted with water so as to have a less than 3% DMSO percentage (v/v) in the incubation mixtures.

Fluorescence measurements were carried out as described by Naiki et al., *Anal. Biochem.* 1989, 177, 244, and by H. LeVine III, *Protein Sci.* 1993, 2, 404. Briefly, the incubated samples were diluted at a peptide concentrartion of 8 mg/ml in 50 mM sodium citrate buffer pH 5 containing 47 mM thioflavin T in a final volume of 1.5 ml. Fluorescence was measured with excitation at 420 nm and emission at 490 nm in a Kontron fluorescence spectrophotometer and the values were averaged after subtracting the background fluorescence of 47 mM ThT.

The results are expressed as relative fluorescence, i.e. the percentage of the fluorescence of the Aβ 25–35 peptide incubated alone (control).

Compounds 1 reduced thioflavin T fluorescence of up to 90% when coincubated with the peptide solution, and their toxicity was found to be quite negligible. The activity of the compounds disclosed in the present patent is also shown by their interference with the seed-triggered aggregation of the Aβ1-40 peptide in monomeric form. The activity of the disclosed compounds is assessed according to the procedure reported below. An Aβ1-40 peptide monomer stock solution is prepared by dissolving the peptide in dimethylsulfoxide at a concentration of 33.33 mg/mL. The stock solution is further diluted 1 to 11.5 with dimethylsulfoxide. This solution is then diluted with 10 mM phosphate buffer pH 7.4 containing 150 mM sodium chloride to prepare the test solution. To an eppendorf tube containing 47 $\mu$L of Aβ1-40 peptide monomer solution are added 3 $\mu$L of a 830 $\mu$M water solution of the test compound containing 66.4 $\mu$M, based on the Aβ1 -40 monomer content, of pre-formed sonicated Aβ1-40 fibrils: the resulting solution is 20 $\mu$M in Aβ1-40 monomer, 50 $\mu$M in the test compound and contains 4 $\mu$M, based on the Aβ1-40 monomer content, of pre-formed sonicated Aβ1-40 fibrils. The aggregation is allowed to proceed for two hours at 37° C. The suspension is then centrifuged at 15000 rpm for 15 minutes at +4° C., the supernatant is collected and the Aβ1-40 monomer is quantitated by HPLC.

The activity of some representative compounds is reported in Table 1. The activity is expressed as the percent of inhibition of the aggregation of a 20 μM Aβ1-40 monomer solution stimulated by 4 μM, based on the Aμ1-40 monomer content, pre-formed sonicated Aμ1-40 fibrils.

TABLE 1

| Compound | % inhibition |
|---|---|
| 1a | 22.9 |
| 1c | 36.0 |
| 1e | 26.2 |
| 1p | 31.7 |
| 1q | 24.2 |
| lac-I | 54.2 |

The compounds of the present invention can be used to make medicaments useful to prevent, to arrest or to slow down the formation of or to induce the degradation of amyloid deposits that are formed by different amyloidogenic proteins. Therefore, the compounds of the present invention can be used in the prevention and in the treatment of different types of amyloidosis diseases. Amyloidosis diseases include peripheral amyloidoses, like AL amyloidosis, and amyloidoses of the central nervous system like Alzheimer's disease, Down Syndrome, spongiform encephalopaties and the like.

The present invention provides a pharmaceutical composition comprising a compound of formula (1) or a pharmaceutically acceptable salt thereof, as active ingredient, in association with a pharmaceutically acceptable carrier, excipient or other additive, if necessary.

Also provided is a compound of formula (I), as defined above, or a pharmaceutically acceptable salt thereof, for use in the treatment of the human or animal body. Further, the present invention provides the use of a compound of formula (I), or a pharmaceutically acceptable salt thereof, in the manufacture of a medicament for use in the treatment of an amyloidosis disease.

The pharmaceutical compositions containing a compound of formula 1 or salts thereof may be prepared in a conventional way by employing conventional non-toxic pharmaceutical carriers or diluents in a variety of dosage forms and ways of administration.

In particular, the compounds of the formula 1 can be administered:
A) orally, for example, as tablets, troches, lozenges, aqueous or oily suspension, dispersible powders or granules, emulsions,
hard or soft capsules, or syrups or elixirs. Compositions intended for oral use may be prepared according to any method known in the art for the manifacture of pharmaceutical compositions and such compositions may contain one or more agents selected from the group consisting of sweetening agents, flavouring agents, coloring agents and preserving agents in order to provide pharmaceutically elegant and palatable preparations.

Tablets contain the active ingredient in admixture with non-toxic pharmaceutically acceptable excipients which are suitable for the manifacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example maize starch, gelatin or acacia, and lubrificating agents, for example magnesium stearate or stearic acid or talc. The tablets may be uncoated or they may be coated by known techniques to delay disintegration and absorpion in the gastrointestinal tract and thereby provide a sustained action over a longer period. For example, a time delay material such as glyceryl monostearate or glyceryl distearate may be employed.

Formulation for oral use may also be presented as hard gelatin capsules wherein the active ingredient is mixed with an inert solid diluent, for example, calcium carbonate, calcium phophate or kaolin, or soft gelatin capsules wherein the active ingredient is mixed with water or an oil medium, for example, peanut oil, liquid paraffin or olive oil. Aqueous suspensions contain the active materials in admixture with excipients suitable for the manifacture of aqueous suspensions.

Such excipients are suspending agents, for example, sodium carboxymethylcellulose, methylcellulose, hydroxy, propylmethyl cellulose, sodium alginate, polyvinylpyrrolidone, gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and a hexitol anhydrides, for example polyoxyethylene sorbitan monooleate.

The said aqueous suspensions may also contain one or more preservatives, for example, ethyl or n-propyl p-hydroxybenzoate, one or more coloring agents, one or more flavouring agents, or one or more sweetening agents, such as sucrose or saccharin. oily suspension may be formulated by suspending the active ingredient in a vegetable oil, for example arachis oil, olive oil, seseme oil or coconut oil or in a mineral oil such as liquid paraffin. The oily suspensions may contain a thickening agent, for example beewax, hard paraffin or cetyl alcohol. Sweetening agents, such as those set forth above, and flavoring agents may be added to provide a palatable oral preparation.

These compositions may be preserved by the addition of an autoxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and agents, may also be present.

The pharmaceutical compositions of the invention may also be in the form of oil-in-water emulsions. The oily phase may be a vegetable oil, for example olive oil or arachis oil, or a mineral oil for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxy ethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents.

B) Parenterally, either subcutaneously or intravenously or intramuscularly, or intrasternally, or by infusion techniques, in the form of sterile injectable aqueous or olagenous suspension. The pharmaceutical compositions may be in the form of a sterile injectable aqueous or olagenous suspensions.

This suspension may be formulated according to the known art using those suitable dispersing of wetting agents and suspending agents which have been above. The sterile injectable preparation may also be a sterile injectable solution or suspension in a non-toxic parenterally-acceptable diluent or solvent for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oils may be conventionally employed including synthetic mono- or diglycerides. In addition fatty acids such as oleic acid find use in the preparation of injectables.

The present invention further provides a method of treating a human or animal, e.g. a mammal, suffering from or susceptible to an amyloidosis disease which method comprises administering thereto a non-toxic and therapeutically effective amount of a compound of the formula 1 or a pharmaceutically acceptable salt thereof.

A typical daily dose is from about 0.1 to about 50 mg per kg of body weight, according to the activity of the specific compound, the age, weight and conditions of the subject to be treated, the type and the severity of the disease, and the frequency and route of administration; preferably, daily dosage levels are in the range of 5 mg to 2 g. The amount of active ingredient that may be combined with the carrier materials to produce a single dosage form will vary depending upon the host treated and the particular mode of administration. For example, a formulation intended for the oral may contain from 5 mg to 2 g of active agent compounded with an appropriate and convenient amount of carrier material which may vary from about 5 to about 95 percent of the total composition. Dosage unit forms will generally contain between from about 5 mg to about 500 mg of the active ingredient.

The following Examples illustrate the invention without limiting it.

EXAMPLE 1

8-N-(3,4-dimethoxybenzyl) anthrazalone oxime (1a)

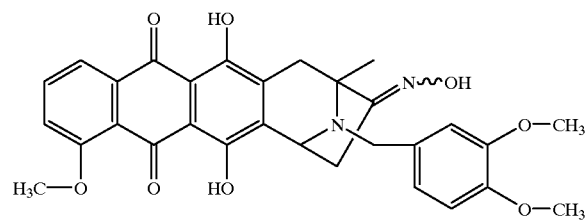

1a

Step 1.

Daunorubicin (3a, 1.58 g, 3 mmol) was dissolved in dry pyridine (20 ml), added with 3,4-dimethoxybenzylamine (2 g, 12 mmol) and kept at room temperature for 16 hours. The reaction mixture was then added with aqueous 1N HCl (400 ml) and extracted with dichloromethane (200 ml). The organic phase was washed with water (2×200 ml), dried over anhydrous sodium sulphate, concentrated to small volume under reduced pressure and flash chromatographed on silica gel using a mixture of toluene-acetone (9:1 by volume) as eluting system to give 1 g of 8-N-(3,4-dimethoxybenzyl) anthrazalone 2a ($R_1$=$OCH_3$, $R_2$=3,4-dimethoxybenzyl). TLC on Kieselgel plate $F_{254}$ (Merck), eluting system dichloromethane-acetone (95:5 by volume) $R_f$=0.56 FAB-MS(+): m/z 530 $[MH]^+$; 380 $[M-CH_2(C_6H_3)(OCH_3)_2+2H]^+$;

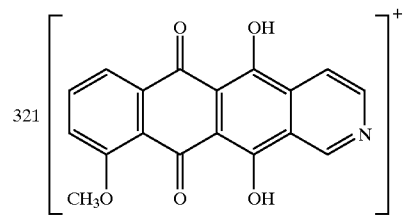

321

$^1$HNMR (400 MHz, CDC$_3$) δ: 1.43 (s, 3H, CH$_3$); 2.34 (d, J=17.5 Hz, 1H, CH(H)-12); 2.66, 2.77 (two doublets, J=19.4Hz, 2H, CH$_2$-10); 2.81 (dd, J=7.3, 17.5 Hz, 1H, CH(H)-12); 3.24, 3.79 (two doublets, J=12.8 Hz, 2H, N—CH$_2$—Ph); 3.85, 3.86 (2xs, 6H, 2xOCH$_3$); 4.08 (s, 3H, 4—OCH$_3$); 4.77 (d, J=7.3 Hz, 1H, H-7); 6.6–6.8 (m, 3H, aromatic hydrogens); 7.38 (d, J=7.6 Hz, 1H, H-3); 7.77 (dd, J=7.6, 7.8 Hz, 1H, H-2); 8.03 (d, J=7.8 Hz, 1H, H-1); 13.22 (s, 1H, OH-11); 13.50 (s, 1H, OH-6).

Step 2.

A solution of 8-N-(3,4-dimethoxybenzyl)anthrazalone 2a (1 g, 1.89 mmol.) in 30 ml of ethanol was treated with hydroxylamine hydrochloride (0.2 g, 2.83 mmol.) and sodium acetate (0.38 g, 2.83 mmol.) and refluxed during three hours. The solvent was evaporated. The residue was taken up with dichloromethane and water, the organic phase was separated and dried over anhydrous sodium sulphate. The solution was concentrated to small volume, diethyl ether was added and the precipitated oxime (1a) was collected: 0.55 g (54% yield).

FAB-MS: m/z 545 [M+H]$^+$; 151 [C$_9$H$_{11}$O$_2$]$^+$ $^1$HNMR (200 MHz, CDCl$_3$) δ: 1.55 (s, 3H, CH$_3$); 2.68 (d, J=16.9 Hz, 1H, CH(H)-12); 2.77, 2.87 (two doublets, J=19.3 Hz, 2H, CH$_2$-10); 2.81 (dd, J=5.7, 16.9 Hz, 1H, CH(H)-12); 3.15, 3.78 (two doublets, J=12.7 Hz, 2H, N—CH$_2$—Ar); 3.83, 3.85 (two singlets, 6H, two OCH$_3$) ; 4.07 (s, 3H, 4-OCH$_3$); 4.60 (d, J=5.7 Hz, 1H, H-7); 6.6–6.8 (m, 3H, aromatic hydrogens); 7.04 (s, 1H, C=NOH); 7.37 (dd, J=1.1, 8.6 Hz, 1H, H-3); 7.76 (dd, J=7.7, 8.6 Hz, 1H, H-2); 8.02 (dd, J=1.1, 7.7 Hz, 1H, H-1); 13.26, 13.51 (two singlets, 2H, phenolic OH).

EXAMPLE 2

8-N-allylanthrazalone oxime (1b)

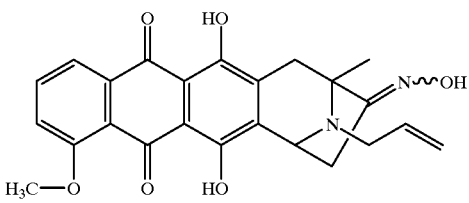

1b

Step 1.

Daunorubici (3a, 1.58 g, 3 mmol) was reacted with allylamine (0.9 g, 12 mmol) as described for the preparation of 2a in Example 1. The crude material was flash chromatographed on silica gel by using a mixture of dichloromethane and acetone (98:2 by volume) as eluting system to give 0.85 g of 8-N-allyl anthrazalone 2b (R$_1$=OCH$_3$, R$_2$=allyl).

TLC on Kieselgel plate F$_{254}$ (Merck), eluting system dichloromethane-acetone (95:5 by volume) R$_f$=0.1

$^1$HNMR (200 MHz, CDCl$_3$) δ: 1.37 (s, 3H, CH$_3$); 2.41 (d, J=17.6 Hz, 1H, CH(H)-12); 2.64 (m, 2H, CH$_2$-10); 2.88 (dd, J=7.2, 17.6 Hz, 1H, CH(H)-12); 2.8–3.4 (m, 2H, CH$_2$CH=CH$_2$); 4.04 (s, 3H, 4-OCH$_3$); 5.0–5.2 (m, 2H, CH$_2$CH=CH$_2$); 5.90 (m, 1H, CH$_2$CH=CH$_2$); 7.37 (d, J=8.4 Hz, 1H, H-3) 7.75 (dd, J=7.6, 8.4 Hz, 1H, H-2); 8.00 (d, J=7.6 Hz, 1H, H-1); 13.0, 13.5 (2xs, 2H, OH-6+OH-11).

Step 2.

A solution of 8-N-allylanthrazalone 2b (1.5 g, 3.58 mmol.) in 30 ml of ethanol was trated with hydroxylamine hydrochloride (0.41 g, 5.8 mmol.) and sodium acetate (0.47 g, 5.8 mmol.) and refluxed during three hours. The solvent was evaporated. The residue was taken up with dichloromethane and water, the organic phase was separated and dried over anhydrous sodium sulphate. The solution was concentrated to small volume, n-exane was added and the precipitated oxime (1b) was collected: 1.2 g (77% yield).

FAB-MS: m/z 435 [M+H]$^+$;

$^1$HNMR (200 MHz, CDCl$_3$) δ: 1.48 (s, 3H, CH$_3$); 2.6–3.0 (m, 5H, CH$_2$-12+CH$_2$-10+CH(H)N); 3.30 (m, 1H, CH(H)N); 4.06 (s, 3H, 4-OCH$_3$); 4.83 (d, J=6.4 Hz, 1H, H-7); 5.02 (d, J=17.1 Hz, 1H, CH=CH(H-trans)); 5.09 (d, J=10.1 Hz, 1H, CH=CH(H-cis)); 5.90 (m, 1H, NCH$_2$CH=CH$_2$); 7.08 (s, 1H, C=N—OH); 7.35 (d, J=8.4 Hz, 1H, H-3); 7.74 (dd, J=7.7, 8.4 Hz, 1H, H-2); 7.99 (d, J=7.7 Hz, 1H, H-1); 13.20, 13.55 (two singlets, 2H, phenolic OH).

EXAMPLE 3

8-N-allylanthrazalone O-methyl-oxime (1c)

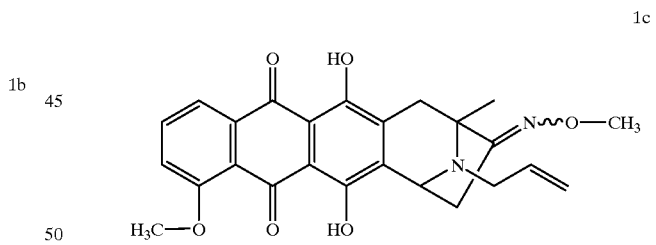

1c

A solution of 8-N-allylanthrazalone 2b, prepared as decribed in the example 2, (0.5 g, 1.19 mmol.) in 15 ml of ethanol was treated with O-methyl-hydroxylamine hydrochloride (0.2 g, 2.38 mmol.) and sodium acetate (0.2 g, 2.38 mmol.) and refluxed during four hours. The solvent was evaporated. The residue was taken up with dichloromethane and water, the organic phase was separated and dried over anhydrous sodium sulphate. The reaction mixture was flash chromatographed on silica gel by using a mixture of cyclohexane-ethyl acetate (80:20 by volume) to give 0.15 g (28% yield) of compound 1c. TLC on Kieselgel plate F$_{254}$ (Merck), eluting system cyclohexane-ethyl acetate (50:50 by volume) R$_f$=0.37. ESI-MS: m/z 449 [M+H]$^+$;

¹HNMR (400 MHz, CDCl₃) δ: 1.50 (s, 3H, CH₃); 2.64 (d, J=17.5 Hz, 1H, CH(H)-12); 2.72, 2.82 (two doublets, J=19.2 Hz 2H, CH₂-10); 2.84 (dd, J=6.8, 17.5 Hz, 1H, CH(H)-12); 2.55, 3.30 (two multiplets, 2H, N—CH₂CH═CH₂); 3.79 (s, 3H, N—OCH₃); 4.07 (s, 3H, 4-OCH₃); 4.80 (d, J=6.8 Hz, 1H, H-7); 5.05 (m, 2H, CH₂CH═CH₂) ; 5.89 (m, 1H, CH₂CH═CH₂); 7.36 (dd, J=0.8, 8.5 Hz, 1H, H-3); 7.75 (dd, J=7.7, 8.5 Hz, 1H, H-2); 8.01 (dd, J=0.8, 7.7 Hz, 1H, H-1); 13.23, 13.56 (two s, 2H, OH-6+OH-11).

Operating as described in the previous examples, the following compounds may be also prepared.

EXAMPLE 4

8-N-allylanthrazalone O-benzyl oxime, 1d
(R₁═OCH₃, R₂═allyl, R₃═OCH₂Ph);

EXAMPLE 5

8-N-(3.4-dimethoxybenzyl)anthrazalone O-methyloxime (1e)

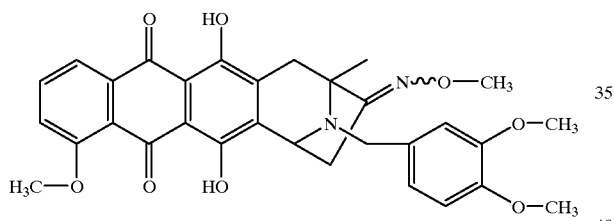

1e

A solution of 8-N-(3,4-dimethoxybenzyl)anthrazalone 2a (1 g, 1.88 mmol.), prepared as decribed in the example 1, in 30 mL of ethanol was treated with O-methylhydroxylamine hydrochloride (0.62 g, 7.42 mmol.) and sodium acetate (1.01 g, 7.42 mmol.) and refluxed during 24 hours. The solvent was evaporated. The residue was taken up with dichloromethane and water, the organic phase was separated, dried over anhydrous sodium sulphate and evaporated. The residue was triturated with diethyl ether and filtered to give 0.69 g (65 % yield) of compound 1e. Compound 1e was transformed into the hydrochloride salt by addition of methanolic hydrochloric acid to a solution of the compound in dichloromethane and precipitation of the hydrochloride salt with diethyl ether.

ESI-MS: m/z 559 [M+H]⁺;

¹HNMR (400 MHz, DMSO-d6, T=55° C.) δ: 1.52 (s, 3H, CH₃) ; 2.2–3.8 (m, 6H, CH₂-12+CH₂-10+NCH₂—Ar); 3.65, 3.70, 3.71 (three singlets, 9H, three OCH₃) ; 3.95 (s, 3H, 4-OCH₃); 4.47 (s, 1H, H-7); 6.7–6.9 (m, 3H, C₆H₃—(OCH₃)₂); 7.60 (m, 1H, H-3); 7.88 (m, 1H, H-1+H-2); 13.00, 13.41 (two singlets, 2H, OH-6+OH-11).

EXAMPLE 6

8-N-(3.4-dimethoxybenzyl)anthrazalone O-benzyloxime (1f)

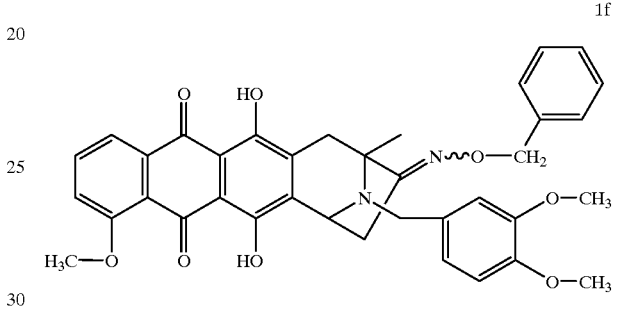

1f

A solution of 8-N-(3,4-dimethoxybenzyl)anthrazalone 2a (0.5 g, 0.94 mmol.), prepared as decribed in the example 1, in 30 mL of ethanol was treated with O-benzylhydroxylamine hydrochloride (0.30 g, 1.88 mmol.) and sodium acetate (0.26 g, 1.88 mmol.) and refluxed during 12 hours. The solvent was evaporated. The residue was taken up with dichloromethane and water, the organic phase was separated, dried over anhydrous sodium sulphate and concentrated to small volume. The reaction mixture was flash chromatographed on silica gel by using a mixture of dichloromethane-acetone (95:5 by volume) to give 0.30 g (50% yield) of compound 1f.

ESI-MS: m/z 635 [M+H]⁺;

¹HNMR (200 MHz, CDCl₃) δ: 1.54 (s, 3H, CH₃); 2.64 (d, J=17.6 Hz, 1H, CH(H)-12); 2.76, 2.88 (two doublets, J=19.3 Hz, 2H, CH₂-10) ; 2.82 (dd, J=5.9, 17.6 Hz, 1H, CH(H)-12); 3.16, 3.77 (two doublets, J=12.7 Hz, 2H, N—CH₂—Ar) ; 3.84, 3.86 (two singlets, 6H, two OCH₃); 4.08 (s, 3H, 4-OCH₃) ; 4.57 (d, J=5.9 Hz, 1H, H-7) ; 5.03 (m, 2H, OCH₂Ph); 6.74 (m, 3H, C₆H₃—(OCH₃)₂); 7.26 (m, 5H, Ph) ; 7.36 (m, 1H, H-3); 7.78(dd, J=9.0 Hz, 1H, H-2); 8.04 (d, J=9.0 Hz, 1H, H-1); 13.29, 13.50 (two singlets, 2H, OH-6+H-11).

EXAMPLE 7

8-N-benzylanthrazalone O-methyl oxime, 1g
($R_1$=OCH$_3$, $R_2$=benzyl, $R_3$=OCH$_3$);

EXAMPLE 8

8-N-benzylanthrazalone O-benzyl oxime, 1h
($R_1$=OCH$_3$, $R_2$=benzyl, $R_3$=OCH$_2$Ph);

EXAMPLE 9

8-N-(4-trifluoromethylbenzyl)anthrazalone O-methyl oxime, 1i ($R_1$=OCH$_3$, $R_2$=4-trifluoromethylbenzyl, $R_3$=OCH$_3$);

EXAMPLE 10

8-N-(4-trifluoromethylbenzyl)anthrazalone O-benzyl oxime, 1l ($R_1$=OCH$_3$, $R_2$=4-trifluoromethylbenzyl, $R_3$=OCH$_2$Ph);

EXAMPLE 11

8-N-(3,5-dit.butyl-4-hydroxybenzyl)anthrazalone oxime, 1m ($R_1$=OCH$_3$, $R_2$=3,5-dit.butyl-4-hydroxybenzyl, $R_3$=OH);

EXAMPLE 12

8-N-(3,5-dit.butyl-4-hydroxybenzyl)anthrazalone O-methyl oxime, 1n ($R_1$=OCH$_3$, $R_2$=3,5-dit.butyl-4-hydroxybenzyl, $R_3$=OCH$_3$);

EXAMPLE 13

8-N-(3,5-dit.butyl-4-hydroxy-benzyl)anthrazalone O-benzyl oxime, 1o ($R_1$=OCH$_3$, $R_2$=3,5-dit.butyl-4-hydroxy-benzyl, $R_3$=OCH$_2$Ph);

EXAMPLE 14

8-N-(4-pyridylmethyl)anthrazalone O-methyloxime (1p)

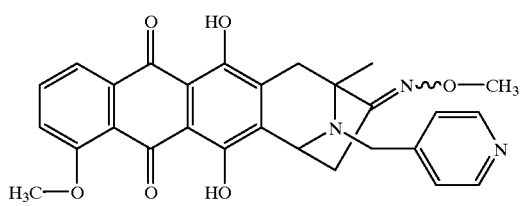

1p

Step 1.

Daunorubicin (3a, 1.58 g, 3 mmol.) was dissolved in dry pyridine (20 mL), added with 4-aminomethylpyridine (1.2 g, 12 mmol.) and kept at room temperature for 16 hours. The reaction mixture was then added with aqueous 1N HCl (400 mL) and extracted with dichloromethane (200 mL). The organic phase was washed with water (2×200 mL), dried over anhydrous sodium sulphate, concentrated to small volume under reduced pressure and flash chromatographed on silica gel using a mixture of toluene-acetone (9:1 by volume) as eluting system to give 0.95 g (67% yield) of 8-N-(4-pyridylmethyl)anthrazalone 2c ($R_1$=OCH$_3$, $R_2$=4-pyridylmethyl).

FAB-MS(+): m/z 471 [MH]$^+$; 380 [M—CH$_2$(C$_5$H$_4$N)+2H]$^+$;

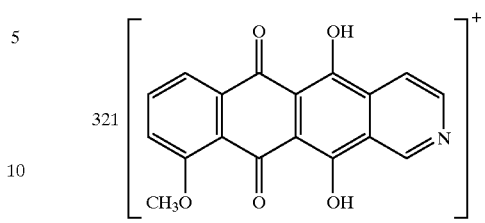

$^1$HNMR (400 MHz, CDCl$_3$) δ: 1.39 (s, 3H, CH$_3$); 2.50 (d, J=17.9 Hz, 1H, CH(H)-12); 2.78 (s, 2H, CH$_2$-10); 2.96 (dd,. J=7.3, 17.9 Hz, 1H, CH(H)-12); 3.70, 4.07 (two doublets, J=16.7 Hz, 2H, N$^+$—CH$_2$—Py); 4.07 (s, 3H, OCH$_3$); 4.76 (d, J=7.3 Hz, 1H, H-7); 7.40 (d, J=7.3 Hz, 1H, H-3); 7.79 (dd, J=7.3 Hz, 1H, H-2); 7.89 (d, J=6.0 Hz, 2H, C$_6$H$_5$N); 8.02 (d, J=7.7 Hz, 1H, H-1); 8.70 (d, J=6.0 Hz, 2H, C$_6$H$_5$N); 13.14 (s, 1H, OH-1l); 13.45 (s, 1H, OH-6).

Step 2.

A solution of 8-N-(4-pyridylmethyl)anthrazalone 2c (0.5 g, 1.06 mmol.) in 30 mL of ethanol was treated with O-methyl hydroxylamine hydrochloride (0.18 g, 2.15 mmol.) and sodium acetate (0.29g, 2.15 mmol.) and refluxed during 12 hours. The solvent was evaporated. The residue was taken up with dichloromethane and water, the organic phase was separated, dried over anhydrous sodium sulphate and concentrated to small volume. The residue was flash chromatographed on silica gel by using a mixture of dichloromethane-acetone (80:20 by volume) to give 0.18 g (34% yield) of compound 1p.

ESI-MS: m/z 500 [M+H]$^+$;

$^1$HNMR (200 MHz, DMSO-d$_6$) δ: 1.41 (s, 3H, CH$_3$); 2.48 (d, J=19.0 Hz, 1H, CH(H)-10); 2.54 (d, J=17.1 Hz, 1H, CH(H)-12); 2.90 (m, 2H, CH(H)-12+CH(H)-10); 3.51, 4.08 (two doublets, J=17.5 Hz, 2H, N—CH$_2$—Py); 3.72 (s, 3H, N—OCH$_3$) ; 3.94 (s, 3H, 4-OCH$_3$); 4.48 (d, J=6.3 Hz, 1H, H-7); 7.60 (m, 2H, C$_5$H$_5$N); 7.84 (m, 2H, H-1+H-2); ); 8.67 (m, 2H, C$_5$H$_5$N); 13.03, 13.48 (two singlets, 2H, OH-6+OH-11).

EXAMPLE 15

8-N-(4-pyridylmethyl)anthrazalone O-benzyloxime (1q)

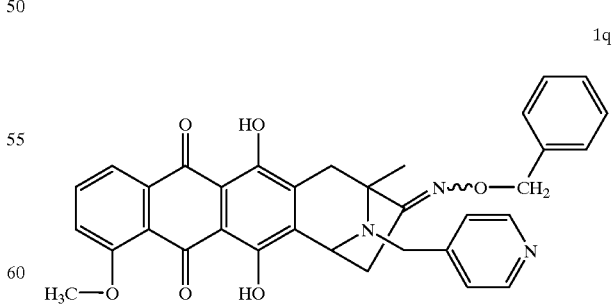

1q

A solution of 8-N-(4-pyridylmethyl)anthrazalone 2c (0.5 g, 1.06 mmol.) in 30 mL of ethanol was treated with O-benzyl hydroxylamine hydrochloride (0.4 g, 2.51 mmol.) and sodium acetate (0.34 g, 2.51 mmol.) and refluxed during 6 hours. The solvent was evaporated. The residue was taken up with dichloromethane and water, the organic phase was separated, dried over anhydrous sodium sulphate and concentrated to small volume. The residue was flash chromatographed on silica gel by using a mixture of dichloromethane-acetone (80:20 by volume) to give 0.19 g (31 yield) of compound 1q.

ESI-MS: m/z 576 [M+H]$^+$;

$^1$HNMR (200 MHz, DMSO-d$_6$) δ: 1.40 (s, 3H, CH$_3$); 2.47 (d, J=17.0 Hz, 1H, CH(H)-12); 2.50, 2.89 (two doublets, J=18.8 Hz, 2H, CH$_2$-10); 2.85 (dd, J=6.8, 17.0 Hz, 1H, CH(H)-12); 3.20, 3.90 (two doublets, J=15.0 Hz, 2H, N—CH$_2$—Py); 3.93 (s, 3H, OCH$_3$); 4.39 (d, J=6.8 Hz, 1H, H-7); 4.96 (s, 2H, OCH$_2$Ph); 7.23 (m, 7H, Ph+C$_5$H$_5$N); 7.60 (m, 1H, H-3); 7.87 (m, 2H, H-1+H-2); 8.43 (dd, J=1.7, 4.3 Hz, 2H, C$_5$H$_5$N); 13.00, 13.40 (broad signals, 2H, OH-6+ OH-11).

EXAMPLE 16

8-N-allylanthrazalone N,N-dimethylhydrazone, 1r (R$_1$=OCH$_3$, R$_2$=allyl, R$_3$=N (CH$_3$)$_2$);

EXAMPLE 17

8-N-(4-pyridinmethyl)anthrazalone, 4-methylpyperazinyl hydrazone, 1s (R$_1$=OCH$_3$, R$_2$= 4-pyridinmethyl, R$_3$=4-methyl-piperazinyl);

EXAMPLE 18

8-N-(4-pyridinmethyl)anthrazalone, 4-morpholinyl hydrazone, 1t (R$_1$=OCH$_3$, R$_2$=4-pyridinmethyl, R$_3$=4-morpholinyl);

EXAMPLE 19

4-Demethoxy-8-N-(4-pyridinmethyl)anthrazalone O-methyl oxime, 1u (R$_1$=H, R$_2$=4-pyridinmethyl, R$_3$=OCH$_3$);

EXAMPLE 20

8-N-(3-bromobenzyl)anthrazalone O-methyl oxime, 1v (R$_1$=OCH$_3$, R$_2$=3-bromobenzyl, R$_3$=OCH$_3$).

EXAMPLE 21

8-N-allylanthrazalone O-ethyloxime (1w)

1w

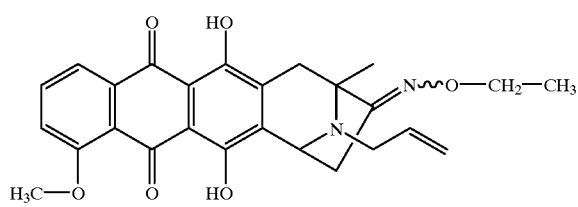

A solution of 8-N-allylanthrazalone 2b (0.6 g, 1.43 mmol.), prepared as decribed in the example 2, in 15 mL of ethanol was treated with O-ethylhydroxylamine hydrochloride (0.27 g, 2.77 mmol.) and sodium acetate (0.36 g, 2.77 mmol.) and refluxed during four hours. The solvent was evaporated. The residue was taken up with dichloromethane and water, the organic phase was separated, dried over anhydrous sodium sulphate and concentrated to small volume. The reaction mixture was flash chromatographed on silica gel by using a mixture of cyclohexane-ethyl acetate (90:10 by volume) to give 0.43 g (65% yield) of compound 1w.

ESI-MS: m/z 463 [M+H]$^+$;

$^1$HNMR (400 MHz, CDl$_3$) δ: 1.18 (t, J=7.0 Hz, 3H, OCH$_2$Ch$_3$); 1.50 (s, 3H, CH$_3$); 2.64 (d, J=16.5 Hz, 1H, CH(H)-12); 2.70, 2.80 (two doublets, J=18.0 Hz 2H, CH$_2$-10); 2.75, 3.30 (two multiplets, 2H, N—CH$_2$CH=CH$_2$); 2.84 (dd, J=6.4, 16.5 Hz, 1H, CH(H)-12); 4.04 (m, 2H, N—OCH$_2$CH$_3$); 4.08 (s, 3H, 4-OCH$_3$); 4.82 (d, J=6.8 Hz, 1H, H-7); 5.10 (m, 2H, CH$_2$CH=CH$_2$); 5.90 (m, 1H, CH$_2$HC=CH$_2$); 7.37 (dd, J=1.1, 8.6 Hz, 1H, H-3); 7.75 (dd, J=7.9, 8.6 Hz, 1H, H-2); 8.02 (dd, J=1.1, 7.9 Hz, 1H, H-1); 13.24, 13.56 (two singlets, 2H, OH-6+OH-11).

EXAMPLE 22

8-N-allylanthrazalone N-methyl hydrazone (1y)

1y

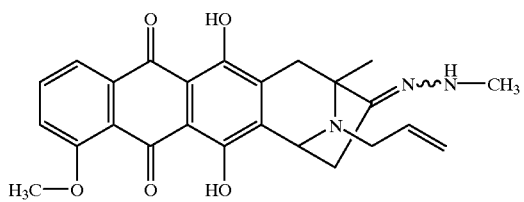

A solution of 8-N-allylanthrazalone 2b (0.5 g, 1.19 mmol.), prepared as decribed in the example 2, in 15 mL of ethanol was treated with N-methyl-hydrazine (0.45 g, 9.52 mmol.) and refluxed during 24 hours. The solvent was evaporated. The residue was taken up with dichloromethane and water, the organic phase was separated, dried over anhydrous sodium sulphate and concentrated to small volume. The reaction mixture was flash chromatographed on silica gel by using a mixture of dichloromethane-methanol (95:5 by volume) to give 0.31 g (58% yield) of compound 1y.

ESI-MS: m/z 448 [M+H]$^+$;

$^1$HNMR (200 MHz, CDCl$_3$) δ: 1.45 (s, 3H, CH$_3$); 2.35 (d, J=16.2 Hz, 1H, C(H)-12); 2.68 (dd, J=6.4, 16.2 Hz 1H, CH(H)-12); 2.72 (m, 2H, CH$_2$-10); 2.70, 3.30 (two multiplets, 2H, N—CH$_2$CH=CH$_2$); 2.88 (s, 3H, NCH$_3$); 4.08 (s, 3H, 4-OCH$_3$); 4.88 (d, J=6.4 Hz, 1H, H-7); 5.10 (m, 2H, CH$_2$CH=CH$_2$); 5.90 (m, 1H, CH$_2$CH$_2$); 7.36 (dd, J=0.9, 8.5 Hz, 1H, H-3); 7.75 (dd, J=7.7, 8.5 Hz, 1H, H-2); 8.01 (dd, J=0.9, 7.7 Hz, 1H, H-1); 13.21, 13.59 (two s, 2H, OH-6+OH-11).

EXAMPLE 23

8-N-(4-pyridylmethyl)anthrazalone O-ethyloxime (1x)

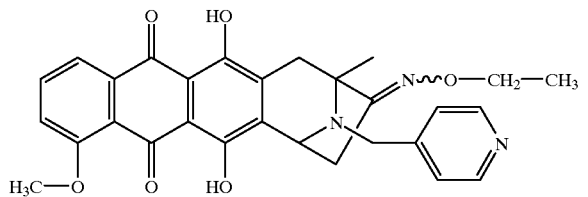

A solution of 8-N-(4-pyridylmethyl)anthrazalone 2c (0.5 g, 1.06 mmol.) in 30 mL of ethanol was treated with 0-ethyl hydroxylamine hydrochloride (0.4 g, 4.1 mmol.) and sodium acetate (0.56 g, 4.1 mmol.) and refluxed during 16 hours. The solvent was evaporated. The residue was taken up with dichloromethane and water, the organic phase was separated, dried over anhydrous sodium sulphate and evaporated. The residue was triturated with a mixture of ethanol and diethyl ether, filtered and washed with the same mixture to give 0.5 g (92% yield) of the title compound 1x.

ESI-MS: m/z 514 [M+H]$^+$;

$^1$HNMR (200 MHz, DMSO-d$_6$) δ: 1.12 (t, J=7.0 Hz, 3H, CH$_3$CH$_2$O); 1.41 (s, 3H, CH$_3$); 2.55, 2.98 (two doublets, J=19.0 Hz, 2H, CH$_2$-10); 2.55 (d, J=17.1 Hz, 1H, CH(H)-12); 2.94 (dd, J=6.4, 17.1 Hz, 1H, CH(H)-12); 3.62, 4.21 (two doublets, J=17.3 Hz, 2H, N—CH$_2$—Py); 3.95 (s, 3H, 4-OCH$_3$); 4.00 (m, 2H, CH$_3$CH$_2$O); 4.48 (d, J=6.4 Hz, 1H, H-7); 7.63 (m, 1H, H-3); 7.86 (m, 4H, H-1+H-2+C$_5$H$_5$N); 8.78 (d, J=6.6 Hz, 2H, C$_5$H$_5$N); 13.04, 13.49 (two singlets, 2H, OQH-6 +OH-11).

EXAMPLE 24

8-N-(4-pyridylmethyl anthrazalone O-(4-pyridylmethyl oxime (1z)

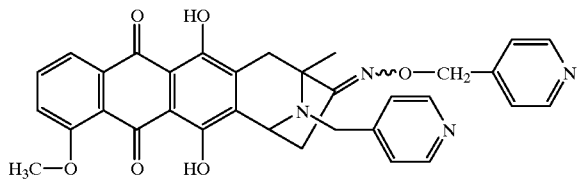

A solution of 8-N-(4-pyridylmethyl)anthrazalone 2c (0.5 g, 1.06 mmol.) in 30 mL of ethanol was treated with O-(4-pyridylmethyl) hydroxylamine hydrochloride (0.42 g, 2.61 mmol.) and sodium acetate (0.36g, 2.61 mmol.) and refluxed during 4 hours. The solvent was evaporated. The residue was taken up with dichloromethane and water, the organic phase was separated, dried over anhydrous sodium sulphate and concentrated to small volume. The residue was flash chromatographed on silica gel by using a mixture of chloroform-methanol (20:1 by volume) to give 0.23 g (38% yield) of compound 1z. The compound was transformed into the hydrochloride salt as described in example 5.

ESI-MS: m/z 577 [M+H]$^+$;

$^1$HNMR (200 MHz, DMSO-d$_6$) δ: 1.38 (s, 3H, CH$_3$); 2.57, 3.00 (two doublets, J=19.0 Hz, 2H, CH$_2$-10); 2.76 (d, J=17.6 Hz, 1H, CH(H)-12); 3.05 (dd, J=6.3, 17.6 Hz, 1H, CH(H)-12); 3.61, 4.16. (two doublets, J=16.6 Hz, 2H, N—CH$_2$—Py); 3.96 (s, 3H, 4-OCH$_3$); 4.56 (d, J=6.3 Hz, 1H, H-7); 5.24 (s, 2H, OCH$_2$Py); 7.60 (m, 3H, H-3+C$_5$H$_5$N); 7.89 (m, 4H, H-1+H-2+C$_5$H$_5$N); 8.67, 8.75 (two doublets, J=6.3 Hz, 4H, C$_5$H$_5$N); 13.05, 13.52 (two singlets, 2H, H-6+OH-11).

EXAMPLE 25

Anthrazalone oxime (1aa)

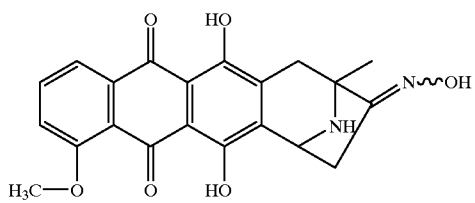

Step 1.

8-N-(3,4-dimethoxybenzyl)-anthrazalone (2a, 1.0 g, 1.89 mmol.) was dissolved in a mixture of methylene chloride (40 mL) and water (2 mL) and treated with 2,3-dichloro-5,6-dicyano-1,4-benzoquinone (DDQ, 0.5 g, 1.89 mmol.) at room temperature. After 4 hours, the reaction mixture was washed with 5% aqueous sodium hydrogen carbonate (3×200 mL) then with water. The organic phase was dried over anhydrous sodium sulphate and the solvent was removed under reduced pressure to afford 0.61 g (85%) of anthrazalone 2d (R$_1$=OCH$_3$, R$_2$=H).

FD-MS: 380 [MH]$^+$; 362 [M—NH$_3$]+

$^1$HNMR (400 MHz, CDCl$_3$) δ: 1.45 (s, 3H, CH$_3$); 2.43 (d, J=17.5 Hz, 1H, CH(H)-12); 2.76, 2.84 (two doublets, J=19.2 Hz, 2H, CH$_2$-10); 2.86 (dd, J=7.3, 17.5 Hz, 1H, CH(H)-12); 4.08 (s, 3H, OCH$_3$); 5.14 (d, J=7.3 Hz, 1H, H-7); 7.37 (d, J=8.5 Hz, 1H, H-3); 7.76 (dd, J=7.7, 8.5 Hz, 1H, H-2); 8.01 (d, J=7.7 Hz, 1H, H-1); 13.14 (s, 1H, OH-11); 13.60 (s, 1H, OH-6).

Step 2.

A solution of anthrazalone 2d (0.5 g, 1.32 mmol.) in 30 mL of ethanol was treated with hydroxylamine hydrochloride (0.14 g, 2 mmol.) and sodium acetate (0.27 g, 2 mmol.) and refluxed during three hours. The solvent was evaporated. The residue was taken up with dichloromethane and water, the organic phase was separated, dried over anhydrous sodium sulphate and concentrated to small volume. The residue was flash chromatographed on silica gel by using a mixture of chloroform-methanol (48:2 by volume) to give 0.06 g (12% yield) of compound 1aa as a 1:1 mixture of E and Z oximes.

ESI-MS: m/z 395 [M+H]$^{30}$ ;

$^1$HNMR (200 MHz, DMSO-d$_6$) δ: 1.43, 1.59 (two singlets, 6H, CH$_3$) ; 2.28, 2.51 (two doublets, J=14.7 Hz, 2H, CH(H)-12 of the two oximes); 2.60, 2.72 (two doublets, J=18.6 Hz, 2H, CH$_2$-10 of one isomer); 2.58, 3.13 (two doublets, J=18.6 Hz, 2H, CH$_2$-10 of the other isomer); 2.68, 2.90 (two doublets, J=7.6, 14.7 Hz, 1H, CH(H)-12 of the two oximes); 3.96 (s, 3H, OCH$_3$); 4.65, 4.68 (two doublets, J=7.6 Hz, 2H, H-7 of the two oximes); 7.64 (m, 1H, H-3); 7.85 (m, 2H, H-1+H-2); 10.45, 10.52 (two singlets, 2H, NOH of the two oximes); 13.00, 13.60 (broad signals, 2H, OH-6+OH-11).

EXAMPLE 26

Anthrazalone O-methyloxime (1ab)

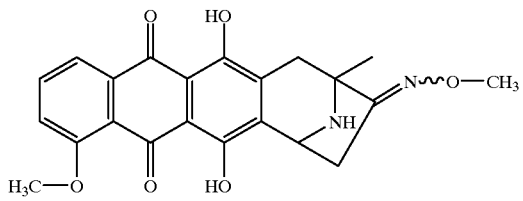

1ab

A solution of anthrazalone 2d (0.5 g, 1.32 mmol.) in 30 mL of ethanol was treated with O-methyl-hydroxylamine hydrochloride (0.33 g, 3.9 mmol.) and sodium acetate (0.53 g, 3.9 mmol.) and refluxed during 12 hours. The solvent was evaporated. The residue was taken up with dichloromethane and water, the organic phase was separated, dried over anhydrous sodium sulphate and concentrated to small volume. The residue was flash chromatographed on silica gel by using a mixture of dichloromethane-acetone (90:10 by volume) to give 0.12 g (23% yield) of compound 1ab.

ESI-MS: m/z 409 [M+H]$^+$;

$^1$HNMR (200 MHz, DMSO-d$_6$) δ: 1.71 (two singlets, 6H, CH$_3$); 2.60 (d, J=15.5 Hz, 1H, CH(H)-12); 2.74, 3.32 (two doublets, J=18.5 Hz, 2H, CH$_2$-10); 3.02 (dd, J=6.2, 15.5 Hz, 1H, CH(H)-12); 3.80 (s, 3H, NOCH$_3$); 4.08 (s, 3H, 4-OCH$_3$); 4.94 (d, J=6.2 Hz, 1H, H-7); 7.37 (dd, J=1.3, 8.6 Hz, 1H, H-3); 7.75 (dd, J=7.7, 8.6 Hz, 1H, H-2); 8.01 (dd, J=1.3, 7.7 Hz, 1H, H-1); 13.22, 13.64 (s, 2H, OH-6+OH-11).

EXAMPLE 27

Anthrazalone O-ethyloxime (1ac) I and II

1ac

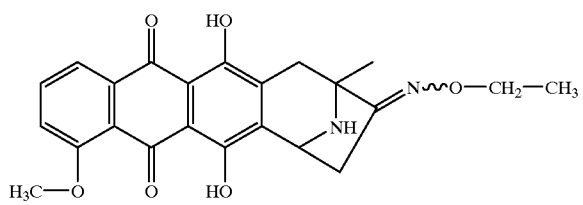

A solution of anthrazalone 2d (0.5 g, 1.32 mmol.) in 30 mL of ethanol was treated with O-ethyl-hydroxylamine hydrochloride (0.51 g, 5.2 mmol.) and sodium acetate (0.71 g, 5.2 mmol.) and refluxed during 24 hours. The solvent was evaporated. The residue was taken up with dichloromethane and water, the organic phase was separated, dried over anhydrous sodium sulphate and concentrated to small volume. The residue was flash chromatographed on silica gel by using a mixture of hexane-ethyl acetate-methanol (50:20:5 by volume) to give 0.085 g (15% yield) of the less polar isomer of compound 1ac-I, m.p. 258–261° C. (dec.) and 0.095 g (17% yield) of the more polar isomer of compound 1ac-II, m.p. 147–149° C.

ESI-MS: m/z 423 [M+H]$^+$;

$^1$H NMR (400 MHz, CDCl$_3$) δ, less polar isomer: 1.19 (t, J=6.8 Hz, 3H, CH$_3$CH$_2$O); 1.60 (s, 3H, CH$_3$); 2.82 (m, 2H, CH$_2$-12); 2.91 (m, 2H, Ch$_2$-10); 4.05 (m, 2H, CH$_3$CH$_2$O); 4.08 (s, 3H, 4-OCH$_3$); 4.97 (m, 1H, H-7); 7.37 (dd, J=1.3, 8.6 Hz, 1H, H-3); 7.76 (dd, J=7.7, 8.6 Hz 1H, H-2); 8.01 (dd, J=1.3, 7.7 Hz, 1H, H-1); 13.19, 13.62 (two singlets, 2H, OH-6+OH-11).

$^1$H NMR (400 MHz, CDCl$_3$) δ, more polar isomer: 1.23 (t, J=7.3 Hz, 3H, CH$_3$CH$_2$O); 1.72 (s, 3H, CH$_3$) ; 2.60 (d, J=15.8 Hz,, 1H, CH(H)-12); 2.74, 3.34 (two doublets, J=18.4 Hz, 2H, CH$_2$-10); 3.02 (dd, J=6.4, 15.8 Hz,, 1H, CH(H)-12); 4.03 (m, 2H, CH$_3$CH$_2$O); 4.08 (s, 3H, 4-OCH$_3$); 4.95 (d, J=6.4 Hz, 1H, H-7); 7.37 (d, J=8.5 Hz, 1H, H-3); 7.76 (dd, J=7.7, 8.5 Hz 1H, H-2); 8.01 (d, J=7.7 Hz, 1H, H-1); 13.23, 13.65 (two singlets, 2H, OH-6+OH-1l).

EXAMPLE 28

Anthrazalone O-benzyloxime (1ad)

1ad

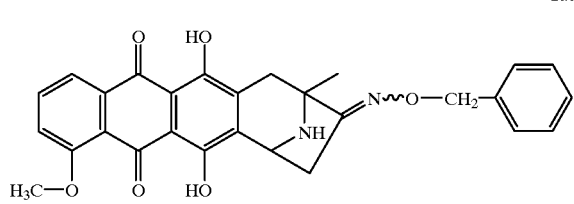

A solution of anthrazalone 2d (0.43 g, 1.13 mmol.) in 30 mL of ethanol was treated with O-benzyl-hydroxylamine hydrochloride (0.36 g, 2.26 mmol.) and sodium acetate (0.31 g, 2.26 mmol.) and refluxed during 16 hours. The solvent was evaporated. The residue was taken up with dichloromethane and water, the organic phase was separated, dried over anhydrous sodium sulphate and evaporated. The residue was triturated with diethyl ether to give 0.28 g (51% yield) of compound 1ad.

ESI-MS: m/z 485 [M+H]$^+$;

$^1$HNMR (200 MHz, DMSO-d,) δ: 1.43 (s, 3H, Ch$_3$); 2.56 (d, J=16.5 Hz, 1H, CH(H)-12); 2.62, 2.76 (two doublets, J=18..0 Hz, 2H, Ch$_2$-10); 2.78 (dd, J=6.1, 16.5 Hz, 1H, CH(H)-12); 3.97 (s, 3H, 4-OCH$_3$); 4.68 (d, J=6.1 Hz, 1H, H-7); 4.97 (s, 2H, CH$_2$Ph); 7.25 (m, 5H, Ph); 7.62 (m, 1H, H-3); 7.87 (m, 2H, H-1+H-2); 13.03, 13.62 (s, 2H, OH-6+OH-11).

EXAMPLE 29

8-N-[2-(4-pyridyl)acetyl]anthrazalone O-methyloxime (1ae)

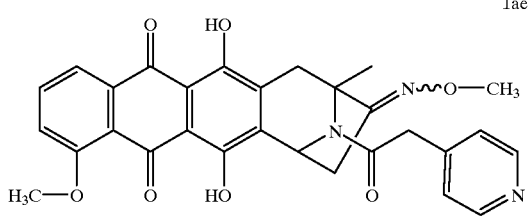

To a solution of anthrazalone O-methyl oxime 1ab (0.117 g, 0.29 mmol.) in 5 mL of anhydrous dichloromethane were added 2-(4-pyridyl) acetic acid (0.05 g, 0.29 mmol.), triethylamine (0.04 mL, 0.29 mmol.) and 4-dimethylaminopyridine (0.017 g, 0.145 mmol.). The reaction mixture was cooled at 0° C and N,N'-diisopropylcarbodiimide (0.051 mL, 0.33 mmol.) was added under stirring. The reaction was stirred five hours at room temperature, poured into a pH 3 buffer solution and extracted twice with dichloromethane. The organic phase was washed with a pH 7 buffer solution and dried over anhydrous sodium sulphate. The solvent was removed under reduced pressure and the residue was triturated with diethyl ether. The solid was collected and washed throughly with diethyl ether to give 0.08 g (52% yield) of the title compound (1ae).

ESI-MS: m/z 528 [M+H]$^+$;

$^1$HNMR (200 MHz, DMSO-d$_6$) δ: 1.92 (s, 3H, CH$_3$); 2.66 (d, J=17.1 Hz, 1H, CH(H)-12); 2.97 (dd, J=6.4, 17.1 Hz, 1H, CH(H)-12); 2.67, 3.35 (two doublets, J=18.2 Hz, 2H, CH$_2$-10); 3.74 (s, 3H, NOCH$_3$); 3.80 (s, 2H, COCH$_2$Py); 3.98 (s, 3H, 4-OCH$_3$) ; 5.69 (d, J=6.4 Hz, 1H, H-7); 7.07 (d, J=5.9 Hz, 2H, C$_5$H$_5$N); 7.66 (m, 1H, H-3); 7.87 (m, 2H, H-1+H-2); 8.20 (d, J=5.9 Hz, 2H, C$_5$H$_5$N); 12.87, 13.40 (s, 2H, OH-6+OH-11).

EXAMPLE 30

8-N-[2-(4-pyridyl)acetyl]anthrazalone O-ethyloxime (1af)

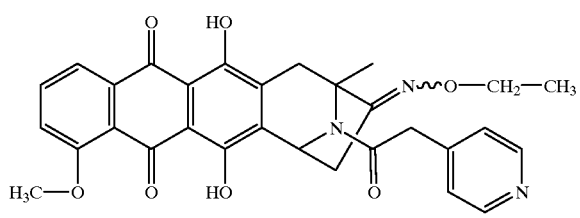

The title compound was prepared as described in Example 28 starting from anthrazalone O-ethyl oxime 1ac (0.15 g, 0.36 mmol.), 2-(4-pyridyl)acetic acid (0.06 g, 0.36 mmol.), triethylamine (0.05 mL, 0.36 mmol.), 4-dimethylaminopyridine (0.02 g, 0.178 mmol.) and N,NI-diisopropylcarbodiimide (0.063 mL, 0.41 mmol.): 0.11 g (57% yield) of compound 1af were obtained.

ESI-MS: m/z 542 [M+H]$^+$;

$^1$HNMR (200 MHz, DMSO-d$_6$) δ: 1.11 (t, J=7.0 Hz, 3H, CH$_3$CH$_2$O); 1.93 (s, 3H, CH$_3$); 2.68 (d, J=16.9 Hz, 1H, CH(H)-12); 2.71, 3.35 (two doublets, J=18.2 Hz, 2H, CH$_2$-10); 2.98 (dd, J=6.6, 16.9 Hz, 1H, CH(H)-12); 3.79 (s, 2H, COCH$_2$Py); 3.98 (s, 3H, 4-OCH$_3$); 3.99 (m, 2H, CH$_3$CH$_2$O); 5.68 (d, J=6.6 Hz, 1H, H-7); 7.07 (d, J=6.1 Hz, 2H, C$_5$H$_5$N); 7.67 (m, 1H, H-3); 7.87 (m, 2H, H-1+H-2); 8.21 (d, J=6.1 Hz, 2H, C$_5$H$_5$N); 13.50 (broad signal, 2H, OH-6+OH-11).

EXAMPLE 31

4-Demethoxy-8-N-(3,4-dimethoxybenzyl) anthrazalone oxime (1ag)

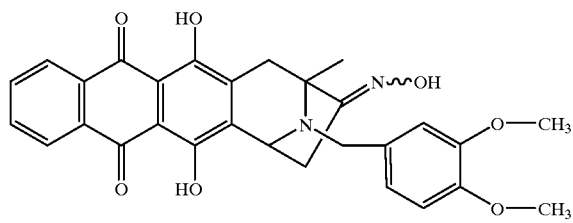

Step 1.

4-Demethoxydaunorubicin (3b, 1.38 g, 3 mmol.) and 3,4-dimethoxybenzylamine (2 g, 12 mmol.) were reacted as described in Example 1 to give 1 g (66% yield) of 4-demethoxy-8-N-(3,4-cdimethoxybenzyl) anthrazalone 2e (R$_1$=H, R$_2$=3,4-dimethoxybenzyl), m.p. 112–115° C.

FAB-MS(+): m/z 500 [MH]$^+$; 350 [M—CH$_2$ (C$_6$H$_3$) (OCH$_3$)$_2$ +2H]$^+$;

Step 2.

A solution of 4-demethoxy-8-N-(3,4-dimethoxybenzyl) anthrazalone 2e (0.5 g, 1 mmol.) in 30 mL of ethanol was treated with hydroxylamine hydrochloride (0.15 g, 2.16 mmol.) and sodium acetate (0.29 g, 2.16 mmol.) and refluxed during 8 hours. The precipitate was filtered, washed with ethanol-water, then with ethanol and dessicated to give 0.4 g (77% yield) of the title compound 1ag.

ESI-MS: m/Z 515 [M+H]$^+$;

$^1$HNMR (200 MHz, CDCl$_3$) δ: 1.55 (s, 3H, Ch$_3$); 2.72 (d, J=17.0 Hz, 1H, C(H)-12); 2.80, 2.92 (two doublets, J=18.4 Hz 2H, Ch$_2$-10); 2.86 (m, 1H, CH(H)-12); 3.19, 3.80 (two doublets, J=12.7 Hz, 2H, NCH$_2$Ar); 3.84, 3.86 (two singlets, 6H, OCH$_3$); 4.61 (d, J=5.7 Hz, 1H, H-7); 6.70 (m, 3H, C$_6$H$_3$-(OCH$_3$)$_2$); 6.90 (s, 1H, NOH); 7.85 (m, 2H, H-2+H-3); 8.35 (m, 2H, H-1+H-4); 13.16, 13.30 (two singlets, 2H, OH-6+OH-11).

EXAMPLE 32

4-Demethoxy-8-N-(3,4-dimethoxybenzyl) anthrazalone O-methyloximne (1ah)

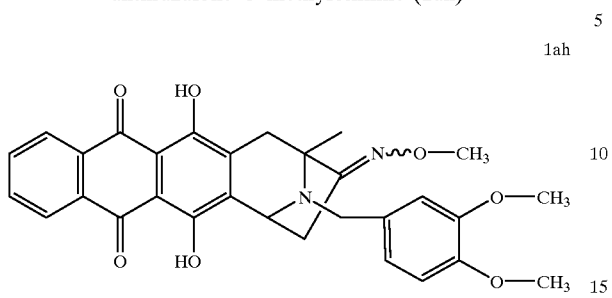

1ah

Operating as described in Example 30, 0.37 g (70% yield) of the title compound 1ah were obtained starting from 4-demethoxy-8-N-(3,4-dimethoxybenzyl) anthrazalone 2e (0.5 g, 1 mmol.), O-methyl hydroxylamine hydrochloride (0.18 g, 2.15 mmol.) and sodium acetate (0.29 g, 2.15 mmol.).

ESI-MS: m/z 529 [M+H]$^+$;

1HNMR (200 MHz, CDCl$_3$) δ: 1.58 (s, 3H, CH$_3$); 2.62 (d, J=17.5 Hz, 1H, C(H)-12); 2.80 (dd, J=6.1, 17.5 Hz, 1H, CH(,H)-12); 2.80, 2.92 (two doublets, J=18.5 Hz, 2H, CH$_2$-10); 3.18, 3.80 (two doublets, J=12.7 Hz, 2H, NCH$_2$Ar); 3.81, 3.84, 3.86 (three singlets, 9H, OCH$_3$) ; 4.58 (d, J=6.1 Hz, 1H, H-7); 6.80 (m, 3H, C$_6$H$_3$-(OCH$_3$)$_2$); 7.85 (m, 2H, H-2+H-3); 8.36 (m, 2H, H-1+H-4); 13.15, 13.30 (two singlets, 2H, OH-6+OH-11).

EXAMPLE 33

Tablets containing the following ingredients may be produced in a conventional manner:

| Ingredient | Per Tablet |
| --- | --- |
| Compound 1 | 25.0 mg |
| Lactose | 125.0 mg |
| Maize starch | 75.0 mg |
| Talc | 4.0 mg |
| Magnesium stearate | 1.0 mg |
| Total weight | 230.0 mg |

EXAMPLE 34

Capsules containing the following ingredients may be produced in a conventional manner:

| Ingredient | Per capsule |
| --- | --- |
| Compound 1 | 50.0 mg |
| Lactose | 165.0 mg |
| Maize starch | 20.0 mg |
| Talc | 5.0 mg |
| Capsule weight | 240.0 mg |

What is claimed is:

1. A compound of the formula (1):

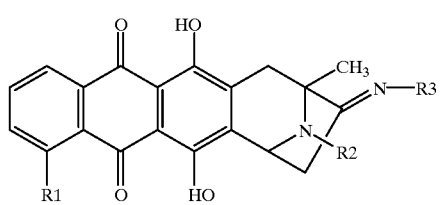

(1)

wherein:
R$_1$ is hydrogen, hydroxy, C$_{1-16}$ alkyl, C$_{1-16}$ alkoxy, or C$_{3-8}$ cycloalkoxy;

R$_2$ is hydrogen, R$_B$—CH$_2$—, wherein R$_B$ is optionally substituted aryl, pyridyl, acetyl, or a group of the formula R$_c$—CH=CH—, wherein R$_c$ is hydrogen, C$_{1-6}$ alkyl, or C$_{3-8}$ cycloalkyl; and R$_3$ is a group of the formula OR$_6$, wherein R$_6$ is hydrogen, C$_{1-16}$ alkyl, C$_{3-8}$ cycloalkyl, or pyridyl; or a pharmaceutically acceptable salt thereof.

2. The compound of claim 1, wherein

R$_1$ is hydrogen, hydroxy, or methoxy;

R$_2$ is hydrogen, benzyl, 3-bromobenzyl, 4-trifluoromethylbenzyl, 4-methoxybenzyl, (4-benzyloxy)benzyl, 3,4-dimethoxybenzyl, 3,5-di-tert-butyl4-hydroxybenzyl, or pyridinemethyl; and R$_3$ is hydroxy, methoxy, ethoxy, or pyridenemethyloxy.

3. The compound of claim 1, which is 8-N-(3, 4dimethyloxybenzyl) anthrazolone oxime or anthrazalone O-ethyloxime, or a pharmaceutically acceptable salt thereof.

4. The compound of claim 1, which is antbizalone O-ethyloxime or a pharmaceutically acceptable salt thereof.

5. A process for preparing a compound of the formula (I), as defined in claim 1, which process comprises:

(a) reacting a compound of the formula (2)

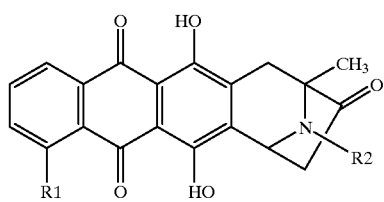

(2)

wherein R$_1$ and R$_2$ are as defined in claim 10, with a compound of the formula:

R$_3$—NH$_2$ wherein R$_3$ is as defmed in claim 10, and (b) optionally converting the thus obtained compound of the formula (1) into another compound of the formula (1); or (c) optionally converting the compound of the formula (1) to a pharmaceutically acceptable salt thereof, or both steps () and (c).

6. The process of claim 5, wherein in step (a) a compound of the formula (2) as defined in claim 5, is reacted with a compound of formula R$_3$—NH$_2$ HA, wherein HA represents an inorganic acid, in an organic solvent in the presence of an organic or inorganic base.

7. The process of claim 6, wherein HA is sulfuric acid or hydrochloric acid.

8. The process of claim 6, wherein said organic solvent is methanol, ethanol, dioxane or toluene.

9. The process of claim 6, wherein said organic base is sodium acetate, and said inorganic base is sodium hydrogen carbonate or potassium hydrogen carbonate.

10. The process of claim 5, which is effected at a temperature of from room temperature to about 100° C.

11. The process of claim 8, which is effected at a temperature of about 80° C., and the solvent is ethanol.

12. A pharmaceutical composition for treating an amyloidosis disease, which comprises, as active ingredient, an effective amount of a compound of the formula (1) as defined in claim 1, or a pharmaceutically acceptable salt thereof, in admixture with a pharmaceutically acceptable carrier or diluent.

13. A method of treating a human or animal suffering from, or susceptible to, an amyloidosis disease, which comprises administering thereto an effective amount of a compound of the formula (1), as defined in claim 1, or a pharmaceutically acceptable salt thereof.

14. The method of claim 11, wherein said amyloidosis disease is AL amyloidosis.

15. The method of claim 11, wherein said amyloidosis disease is Alzheimer's disease.

16. The method of claim 11, wherein said amnyloidosis disease is Down's syndrome.

\* \* \* \* \*